US012685515B2

(12) United States Patent
    Pereira

(10) Patent No.: US 12,685,515 B2
(45) Date of Patent: Jul. 21, 2026

(54) ANALOG PLATFORM FOR INTRAVASCULAR IMAGE ACQUISITION

(71) Applicant: Boston Scientific Scimed Inc., Maple Grove, MN (US)

(72) Inventor: Canute Paul Pereira, Ogilvie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 52 days.

(21) Appl. No.: 18/399,099

(22) Filed: Dec. 28, 2023

(65) Prior Publication Data

US 2024/0215959 A1 Jul. 4, 2024

Related U.S. Application Data

(60) Provisional application No. 63/436,241, filed on Dec. 30, 2022.

(51) Int. Cl.
    *A61B 8/00* (2006.01)
    *A61B 8/08* (2006.01)
    *A61B 8/12* (2006.01)
    *G01S 7/52* (2006.01)
    *G01S 15/89* (2006.01)

(52) U.S. Cl.
    CPC .............. *A61B 8/54* (2013.01); *A61B 8/0891* (2013.01); *A61B 8/12* (2013.01); *A61B 8/4461* (2013.01); *G01S 7/52033* (2013.01); *G01S 15/8934* (2013.01)

(58) Field of Classification Search
    CPC ........... A61B 8/54; A61B 8/0891; A61B 8/12;
    A61B 8/4461; A61B 8/445; G01S 7/52033; G01S 15/8934; G01S 7/52025; G01S 15/8922; G01S 15/894
    See application file for complete search history.

(56) References Cited

U.S. PATENT DOCUMENTS

| | | | | |
|---|---|---|---|---|
| 9,330,624 B1 * | 5/2016 | Pei | ......................... | H03F 3/2173 |
| 2007/0085606 A1 * | 4/2007 | Thomas | ............. | G01N 29/4463 |
| | | | | 330/254 |

(Continued)

FOREIGN PATENT DOCUMENTS

| | | | | |
|---|---|---|---|---|
| CN | 101803111 A | * | 8/2010 | ............. H01P 1/218 |
| JP | H02143185 A | | 6/1990 | |

(Continued)

OTHER PUBLICATIONS

Jonveaux, "A Low-Cost, Arduino-Like Development Kit for Single-Element Ultrasound Imaging," Journal of Open Hardware, vol. 1 No. 1 Cornell University Library, pp. 1-10, Feb. 13, 2017.

(Continued)

*Primary Examiner* — Kaitlyn E Sebastian
(74) *Attorney, Agent, or Firm* — Seager Tufte & Wickhem, LLP

(57) ABSTRACT

A circuit and design for an analog front end is provided. The AFE includes a number of sub-stages each with multiple optional or alternative pathways to complete the circuit. These pathways can be dynamically set during runtime based on the type of imaging catheter used with the AFE or can be set at manufacturing.

17 Claims, 10 Drawing Sheets

(56) References Cited

U.S. PATENT DOCUMENTS

| | | | |
|---|---|---|---|
| 2007/0273354 A1* | 11/2007 | Subhash | H03F 1/304 |
| | | | 323/353 |
| 2008/0310456 A1* | 12/2008 | Bauwelinck | H04B 3/54 |
| | | | 370/488 |
| 2009/0002073 A1* | 1/2009 | Kim | H03G 11/002 |
| | | | 330/279 |
| 2018/0231413 A1 | 8/2018 | Franchitti et al. | |
| 2020/0150252 A1* | 5/2020 | Chen | G01S 7/52025 |
| 2021/0330295 A1* | 10/2021 | Soleimani | G10K 11/346 |

FOREIGN PATENT DOCUMENTS

| | | | |
|---|---|---|---|
| JP | H08145967 A | * | 6/1996 |
| JP | 2001161682 A | | 6/2001 |
| JP | 2009511903 A | | 3/2009 |
| JP | 4814428 B2 | | 11/2011 |
| WO | 2007047015 A2 | | 4/2007 |
| WO | 2017095985 A1 | | 6/2017 |

OTHER PUBLICATIONS

International Search Report and Written Opinion dated Apr. 19, 2024 for International Application No. PCT/US2023/086221.

* cited by examiner

ANALOG PLATFORM FOR INTRAVASCULAR IMAGE ACQUISITION

CROSS-REFERENCE TO RELATED APPLICATIONS

This application claims the benefit of U.S. Provisional Patent Application Ser. No. 63/436,241 filed Dec. 30, 2022, the disclosure of which is incorporated herein by reference.

TECHNICAL FIELD

The present disclosure pertains to medical devices and/or medical device systems. More particularly, the present disclosure pertains to conditioning ultrasound signals for digital processing.

BACKGROUND

A wide variety of intracorporeal medical devices have been developed for medical use, for example, intravascular use. Some of these devices include guidewires, catheters, and the like. A subset of these devices include ultrasound transducers configured to generate ultrasound signals that can be used to recreate images of the vessel. There is an ongoing need to preprocess these signals prior to digitization. However, due to the variety of devices configured to intravascular ultrasound and the various signal qualities these devices support; there is a need provide an analog topology to preprocess intravascular ultrasound signals that support legacy devices and improved devices.

BRIEF SUMMARY

An analog platform, which can be implemented as an analog front end (AFE) in an ultrasound image acquisition system, such as, to acquire intravascular ultrasound signals and generate images from the signals. Of note, the present disclosure provides an AFE that can be used to acquire ultrasound signals from legacy ultrasound catheter devices in addition to allowing for acquisition of ultrasound signals with higher resolution and/or quality than legacy systems. Said differently, the provided AFE includes a number of sub-stages each with multiple pathways through the sub-stage. These pathways can be dynamically set during run-time based on the type of imaging catheter used with the AFE or can be set at manufacturing. However, of note, setting the pathways at manufacturing does not require modification of the circuit or circuit board itself. As such, analog platforms implemented according to the present disclosure provide both backwards compatibility and future proofing.

With some examples, the present disclosure can be implemented as an analog front end (AFE) for an intracorporeal image acquisition device. The AFE can comprise a high-pass filter stage, a gain stage, and a low-pass filter stage. The high-pass filter stage can comprise a plurality of high-pass filters and at least one switch selectable to electrically couple one of the plurality of high-pass filters to an input. The gain stage can comprise: a plurality of voltage attenuators, a plurality of amplifiers circuits, and a plurality of jumper locations, wherein one or more jumpers are installed in at least one but not all of the plurality of jumper locations to electrically couple one of the plurality of voltage attenuators to an output from the high-pass filter stage and to electrically couple an output from the one of the plurality of voltage attenuators to a one of the plurality of amplifier circuits. The low-pass filter stage can comprise a plurality of low-pass filters and at least one switch selectable to electrically couple one of the plurality of low-pass filters to an output from the gain stage.

In further examples of the AFE, the plurality of high-pass filters can comprise a first high-pass filter and a second high-pass filter, wherein the first high-pass filter is between a 0 and 12 megahertz high-pass filter, and wherein the second high-pass filter is between a 15 and 30 megahertz high-pass filter.

In further examples of the AFE, at least one switch of the high-pass filter stage can comprises a first switch and a second switch and wherein the first switch and the second switch are configured to be dynamically controlled by a controller circuit and arranged to electrically couple the input to the analog front end to a selected one of either the first high-pass filter or the second high-pass filter and to electrically couple the output from the selected one of either the first high-pass filter or the second high-pass filter to the output of the high-pass filter stage.

In further examples of the AFE, wherein the first high-pass filter and the second high-pass filter are T high-pass filters comprising a pair of capacitors in arranged in series and an inductor electrically coupled between ground and the center of the pair of capacitors.

In further examples of the AFE, the plurality of voltage attenuators of the gain stage can comprise a first voltage attenuator and a second voltage attenuator, wherein the first voltage attenuator is a 12 decibel voltage attenuator, and wherein the second voltage attenuator is a 28 decibel voltage attenuator.

In further examples of the AFE, the gain stage further comprises a digital to analog converter and at least one transimpedance amplifier, wherein the transimpedance amplifier is electrically coupled to a control input of either the first voltage attenuator or the second voltage attenuator based on the one or more jumpers.

In further examples of the AFE, the plurality of amplifier circuits comprises a first amplifier circuit and a second amplifier circuit, wherein the first amplifier circuit comprises an inductor, an operation amplifier (op-amp), and a plurality of resistors arranged to form an amplifier circuit, and wherein the second amplifier circuit comprises an op-amp and a plurality of resistors arranged to form an amplifier circuit.

In further examples of the AFE, the plurality of voltage attenuators can comprise a first pair of voltage attenuators and a second pair of voltage attenuators and wherein one of the amplifier circuits is electrically coupled between the first one of the first pair of voltage attenuators and a first one of the second pair of voltage attenuators based on the one or more jumpers.

In further examples of the AFE, the gain stage can comprise a first gain stage and a second gain stage, wherein the second gain stage comprises a clipping operational amplifier (op-amp).

In further examples of the AFE, the second gain stage further comprises a first amplifier circuit, a second amplifier circuit, and a plurality of pairs of jumper locations, wherein a pair of jumpers are installed in one of the plurality of pairs of jumper locations to electrically couple an input to the second gain stage to either a selected one of the first amplifier or the second amplifier and to electrically couple the output of the selected one of the first amplifier or the second amplifier to the clipping op-amp.

In further examples of the AFE, the plurality of low-pass filters can comprise a first low-pass filter and a second low-pass filter, wherein the first low-pass filter is less than or equal to a 60 megahertz low-pass filter, and wherein the second low-pass filter is greater than a 60 megahertz low-pass filter.

In further examples of the AFE, the AFE comprises at least one analog to digital converter (ADC) drivers.

With some examples, the present disclosure can be implemented as an intracorporeal image acquisition device comprising image acquisition circuitry comprising the AFE of any of the preceding examples and digital processing circuitry arranged to receive a digitized signal from the AFE and generate an image.

In further examples, the intracorporal image acquisition device can comprise a motor drive unit (MDU) coupled to the image acquisition circuitry.

In further example, the intracorporeal image acquisition device can comprise an intravascular ultrasound catheter coupled to the MDU.

With some examples, the present disclosure can be implemented as an intracorporeal image acquisition device comprising image acquisition circuitry comprising an analog front end (AFE) and a digital processing circuit coupled to the AFE. The digital processing circuit is arranged to receive a digitized signal from the AFE. The AFE can comprise a high-pass filter stage, a gain stage, and a low-pass filter stage. The high-pass filter stage can comprise a plurality of high-pass filters and at least one switch selectable to electrically couple one of the plurality of high-pass filters to an input. The gain stage can comprise a plurality of voltage attenuators, a plurality of amplifiers circuits, and a plurality of jumper locations, wherein one or more jumpers are installed in at least one but not all of the plurality of jumper locations to electrically couple one of the plurality of voltage attenuators to an output from the high-pass filter stage and to electrically couple an output from the one of the plurality of voltage attenuators to a one of the plurality of amplifier circuits. The low-pass filter stage can comprise a plurality of low-pass filters and at least one switch selectable to electrically couple one of the plurality of low-pass filters to an output from the gain stage.

In further examples of the intracorporeal image acquisition device, the plurality of high-pass filters can comprise a first high-pass filter and a second high-pass filter, wherein the first high-pass filter is between a 0 and 12 megahertz high-pass filter, and wherein the second high-pass filter is between a 15 and 30 megahertz high-pass filter.

In further examples of the intracorporeal image acquisition, at least one switch of the high-pass filter stage comprises a first switch and a second switch and wherein the first switch and the second switch are configured to be dynamically controlled by a controller circuit and arranged to electrically couple the input to the analog front end to a selected one of either the first high-pass filter or the second high-pass filter and to electrically couple the output from the selected one of either the first high-pass filter or the second high-pass filter to the output of the high-pass filter stage.

In further examples of the intracorporeal image acquisition device, the first high-pass filter and the second high-pass filter are T high-pass filters can comprise a pair of capacitors in arranged in series and an inductor electrically coupled between ground and the center of the pair of capacitors.

In further examples of the intracorporeal image acquisition device, the plurality of voltage attenuators of the gain stage can comprise a first voltage attenuator and a second voltage attenuator, wherein the first voltage attenuator is a 12 decibel voltage attenuator, and wherein the second voltage attenuator is a 28 decibel voltage attenuator.

With some examples, the present disclosure can be implemented as a system for intracorporeal image acquisition. The system can comprise an intravascular ultrasound (IVUS) catheter, a motor drive unit (MDU) couplable to the IVUS catheter, the MDU arranged to rotate the IVUS catheter during operation, and image acquisition circuitry couplable to the MDU. The image acquisition circuitry is arranged to receive signals comprising indications of ultrasound from the IVUS catheter via the MDU during operation. The image acquisition circuitry can comprise an analog front end (AFE) arranged to receive the signals comprising indications of ultrasound from the IVUS catheter and a digital processing circuit coupled to the AFE, the digital processing circuit arranged to receive a digitized signal from the AFE, the digitized signal based in part on the signals comprising indications of ultrasound from the IVUS catheter. The AFE can comprise a high-pass filter stage, a gain stage, and a low-pass filter stage. The high-pass filter stage can comprise a plurality of high-pass filters and at least one switch selectable to electrically couple one of the plurality of high-pass filters to an input. The gain stage can comprise a plurality of voltage attenuators, a plurality of amplifiers circuits, and a plurality of jumper locations, wherein one or more jumpers are installed in at least one but not all of the plurality of jumper locations to electrically couple one of the plurality of voltage attenuators to an output from the high-pass filter stage and to electrically couple an output from the one of the plurality of voltage attenuators to a one of the plurality of amplifier circuits. The low-pass filter stage can comprise a plurality of low-pass filters and at least one switch selectable to electrically couple one of the plurality of low-pass filters to an output from the gain stage.

In further examples of the system, the plurality of low-pass filters can comprise a first low-pass filter and a second low-pass filter, wherein the first low-pass filter is less than or equal to a 60 megahertz low-pass filter, and wherein the second low-pass filter is greater than a 60 megahertz low-pass filter.

In further examples of the system, the plurality of voltage attenuators can comprise a first pair of voltage attenuators and a second pair of voltage attenuators and wherein one of the amplifier circuits is electrically coupled between the first one of the first pair of voltage attenuators and a first one of the second pair of voltage attenuators based on the one or more jumpers.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Numerous imaging modalities exist to assess vascular lesions, for example, magnetic resonance imaging (MRI), computerized tomography (CT), intravascular ultrasound (IVUS), optical coherence tomography (OCT), optical coherence elastography (OCE) and spectroscopy can give insight to the degree that a vascular lesion varies from healthy tissue. The present disclosure is directed to IVUS signal acquisition and image generate and particularly to analog processing of acquired signals prior to digitization.

Figure 1:
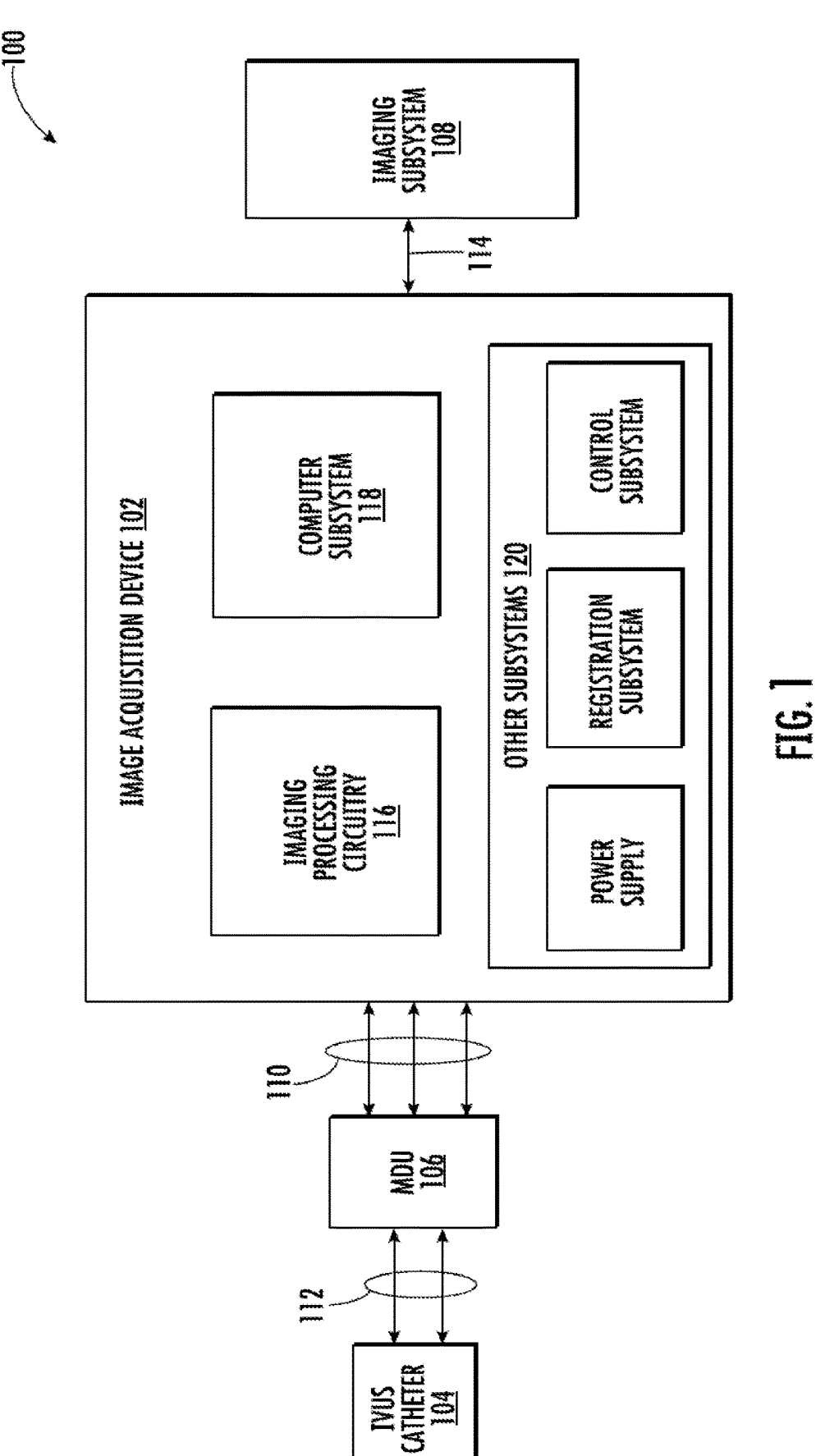
FIG. 1 illustrates an embodiment of an intravascular imaging system.

FIG. 1 illustrates an example IVUS imaging system 100. The IVUS imaging system 100 includes an image acquisition device 102, an IVUS catheter 104, a motor drive unit (MDU) 106, and an imaging subsystem 108. The image acquisition device 102 is coupled to the IVUS catheter 104 via the MDU 106 and is also coupled to the 108. In particular, the image acquisition device 102 is coupled to the MDU 106 via the MDU bus 110 while the MDU 106 is coupled to the IVUS catheter 104 via the catheter bus 112. In some embodiments, the MDU bus 110 and the catheter bus 112 can be transmission lines (or other conductors) arranged to convey signals between the various components. For example, the MDU bus 110 and catheter bus 112 can be arranged to transmit radio frequency signals (e.g., control signals, ultrasound pulse generation signals, ultrasound signals, or the like) between the indicated components of the IVUS imaging system 100.

In general, the image acquisition device 102 is configured to control the MDU 106 and receive signals from the IVUS catheter 104, via the MDU 106. Further, the image acquisition device 102 is configured to process the received signals to generate images and convey the images to the imaging subsystem 108. To that end, the image acquisition device 102 is coupled to the imaging subsystem 108 via the imaging subsystem bus 114, which can be a wired connection or a wireless connection. As a specific example, imaging subsystem bus 114 can be an Ethernet connection. In some examples, the imaging subsystem 108 can be a display, a tablet computer, or other device configured to display images rendered by image acquisition device 102. It is noted that although the imaging subsystem 108 is depicted external to image acquisition device 102, with some embodiments, imaging subsystem 108 can be incorporated into the same housing as image acquisition device 102.

The image acquisition device 102 includes an imaging processing circuitry 116, computer subsystem 118, and other subsystems 120. As indicated above, the present disclosure provides an improved analog platform, which can be implemented as part of the image acquisition device 102, and particularly as part of the imaging processing circuitry 116.

However, a general description of the components of the IVUS imaging system 100 and the image acquisition device 102 is provided prior to detailing the AFE with which the present disclosure is directed. Further it is noted that the image acquisition device 102 can be provided to capture intracorporeal images. Although IVUS images are frequently referenced herein, the circuitry of the present disclosure can be provided as part of an image acquisition device 102 coupled to other modalities of intracorporeal image capture.

Figures 2A, 2B:
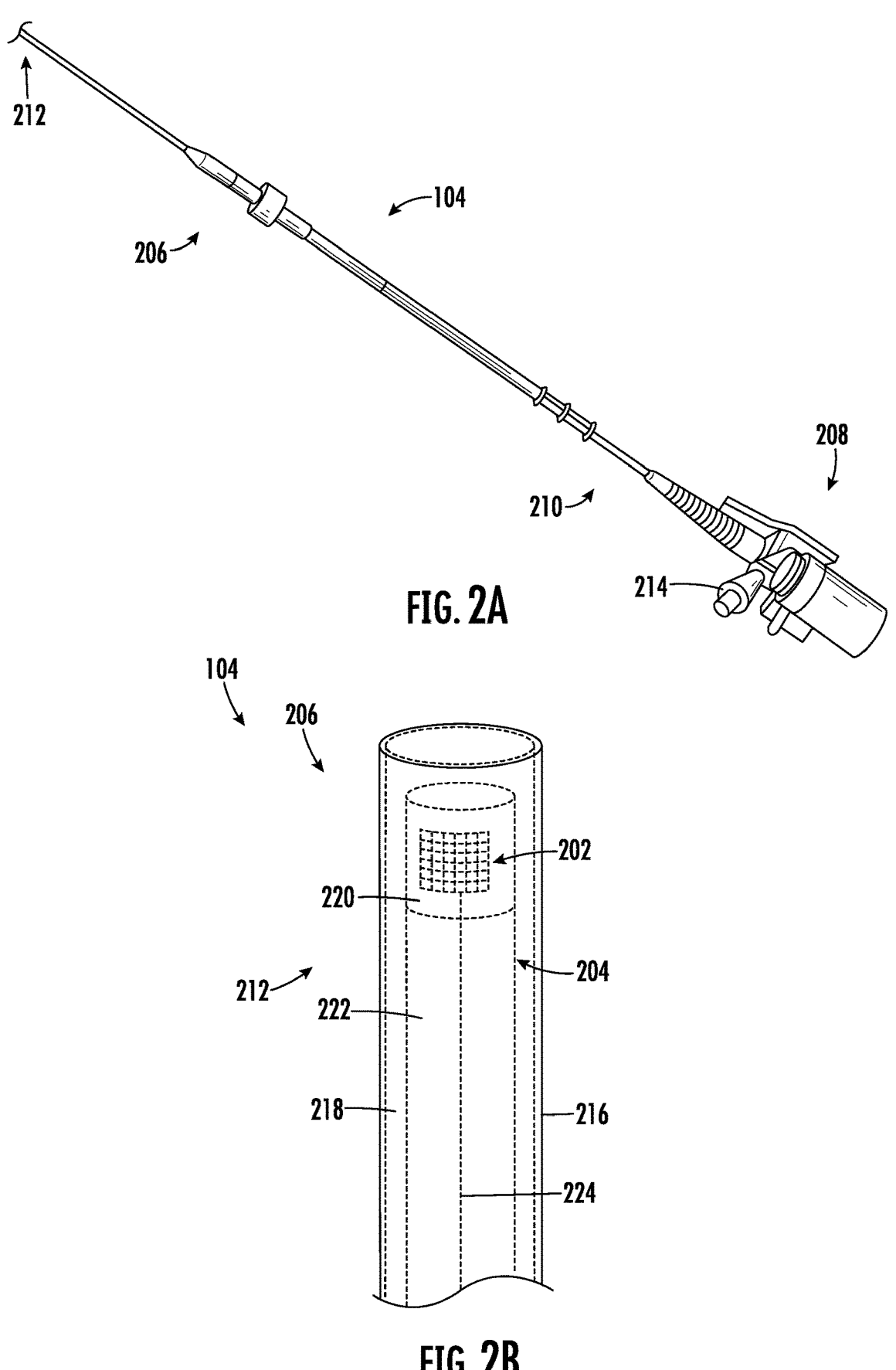
FIG. 2A illustrates an embodiment of portions of the intravascular imaging system of FIG. 1 in greater detail.
FIG. 2B illustrates an embodiment of another portion of the intravascular imaging system of FIG. 1 in greater detail.

FIG. 2A and FIG. 2B illustrate a side and perspective view of the IVUS catheter 104 of the IVUS imaging system 100 of FIG. 1. The other subsystems 120 is configured to power MDU 106 and send signal to IVUS catheter 104 and particularly one or more transducers 202 disposed in the IVUS catheter 104 to cause the IVUS catheter 104 to emit ultrasound signals.

Further, mechanical energy from MDU 106 may be used to drive an imaging core 204 disposed in the IVUS catheter 104. The one or more transducers 202 are further configured to receive reflected signals (e.g., echo signals, or the like) responsive to emitting ultrasound signals. These reflected signals are transmitted to image acquisition device 102 via catheter bus 112, the MDU 106, and MDU bus 110 for processing by imaging processing circuitry 116 and computer subsystem 118.

In some embodiments, other subsystems 120 can be configured to control at least one of the frequency or duration of the electrical pulses transmitted from image acquisition device 102 to MDU 106 to control, for example, the rotation rate of the imaging core 204 by the MDU 106 or the velocity or length of the pullback of the imaging core 204 by the MDU 106.

The IVUS catheter 104 includes an elongated member 206 and a hub 208. The elongated member 206 includes a proximal end 210 and a distal end 212. The proximal end 210 of the elongated member 206 can be coupled to the hub 208 and the distal end 212 of the elongated member 206 is configured and arranged for percutaneous insertion into a patient. Optionally, the IVUS catheter 104 may define at least one flush port, such as flush port 214. The flush port 214 may be defined in the hub 208. The hub 208 may be configured and arranged to couple to the MDU 106 of IVUS imaging system 100.

In some instances, the elongated member 206 and the hub 208 are formed as a unitary body. In other instances, the elongated member 206 and the catheter hub 208 are formed separately and subsequently assembled.

FIG. 2B is a perspective view of one embodiment of the distal end 212 of the elongated member 206 of the IVUS catheter 104. The elongated member 206 includes a sheath 216 with a longitudinal axis (e.g., a central longitudinal axis extending axially through the center of the sheath 216 and/or the IVUS catheter 104) and a lumen 222. An imaging core 224 is disposed in the lumen 218. The imaging core 204 includes an imaging device 220 coupled to a distal end of a driveshaft 222 that is rotatable either manually or using a computer-controlled drive mechanism (e.g., MDU 106). The one or more transducers 202 may be mounted to the imaging device 220 and employed to transmit and receive acoustic signals. The sheath 216 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

In some embodiments, for example as shown in these figures, an array of transducers 202 are mounted to the imaging device 220. Alternatively, a single transducer may be employed. Any suitable number of transducers 202 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used. When a plurality of transducers 202 are employed, the transducers 202 can be configured into any suitable arrangement including, for example, an annular arrangement, a rectangular arrangement, or the like.

The one or more transducers 202 may be formed from materials capable of transforming applied electrical pulses to pressure distortions on the surface of the one or more transducers 230, and vice versa. Examples of suitable materials include piezoelectric ceramic materials, piezocomposite materials, piezoelectric plastics, barium titanates, lead zirconate titanates, lead metaniobates, polyvinylidene fluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like).

The pressure distortions on the surface of the one or more transducers 202 form acoustic pulses of a frequency based on the resonant frequencies of the one or more transducers 202. The resonant frequencies of the one or more transducers 202 may be affected by the size, shape, and material used to form the one or more transducers 202. The one or more transducers 202 may be formed in any shape suitable for positioning within the IVUS catheter 104 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 202 may include a layer of piezoelectric material sandwiched between a matching layer and a conductive backing material formed from an acoustically absorbent material (e.g., an epoxy substrate with tungsten particles). During operation, the piezoelectric layer may be electrically excited to cause the emission of acoustic pulses.

The one or more transducers 202 can be used to form a radial cross-sectional image of a surrounding space. Thus, for example, when the one or more transducers 202 are disposed in the IVUS catheter 104 and inserted into a blood vessel of a patient, the one more transducers 202 may be used to capture acoustic signals to be processed by image acquisition device 102, and particularly by the AFE described herein.

The imaging core 204 is rotated about the longitudinal axis of the IVUS catheter 104. As the imaging core 204 rotates, the one or more transducers 202 emit acoustic signals in different radial directions (e.g., along different radial scan lines). For example, the one or more transducers 202 can emit acoustic signals at regular (or irregular) increments, such as 256 radial scan lines per revolution, or the like. It will be understood that other numbers of radial scan lines can be emitted per revolution, instead.

When an emitted acoustic pulse with sufficient energy encounters one or more medium boundaries, such as one or more tissue boundaries, a portion of the emitted acoustic pulse is reflected to the emitting transducer as an echo pulse. Each echo pulse that reaches a transducer with sufficient energy to be detected is transformed to an electrical signal in the receiving transducer. The one or more transformed electrical signals are transmitted to the imaging processing circuitry 116 of image acquisition device 102 where it is processed and digitized. The digitized signals can be communicated to computer subsystem 118 and used to form images of the vessel, which images can be displayed on imaging subsystem 108. In some instances, the rotation of the imaging core 204 is driven by the MDU 106, which itself is controlled by other subsystems 120.

When the one or more transducers 202 are rotated about the longitudinal axis of the IVUS catheter 104 emitting acoustic pulses, a plurality of images can be formed that collectively form a radial cross-sectional image (e.g., a tomographic image) of a portion of the region surrounding the one or more transducers 202, such as the walls of a blood vessel of interest and tissue surrounding the blood vessel. The imaging core 204 may also move longitudinally along the blood vessel within which the IVUS catheter 104 is inserted so that a plurality of cross-sectional images may be formed along a longitudinal length of the blood vessel. During an imaging procedure the one or more transducers 202 may be retracted (e.g., pulled back) along the longitudinal length of the IVUS catheter 104. The IVUS catheter 104 can include at least one telescoping section that can be retracted during pullback of the one or more transducers 202. In some instances, the MDU 106 drives the pullback of the imaging core 204 within the IVUS catheter 104. The MDU 106 pullback distance of the imaging core 204 can be any suitable distance including, for example, at least 5 cm, 10 cm, 15 cm, 20 cm, 25 cm, or more. The entire IVUS catheter 104 can be retracted during an imaging procedure either with or without the imaging core 204 moving longitudinally independently of the IVUS catheter 104.

The quality of an image produced at different depths from the one or more transducers 202 may be affected by one or more factors including, for example, bandwidth, transducer focus, beam pattern, as well as the frequency of the acoustic pulse. The frequency of the acoustic pulse output from the one or more transducers 202 may also affect the penetration depth of the acoustic pulse output from the one or more transducers 202. In general, as the frequency of an acoustic pulse is lowered, the depth of the penetration of the acoustic pulse within patient tissue increases. In some instances, the intravascular treatment IVUS imaging system 100 operates within a frequency range of 5 MHz to 200 MHZ.

One or more conductors 224 can electrically couple the transducers 202 and catheter bus 112. In such a manner, the electrical signals captured by the transducer 202 can be received by the imaging processing circuitry 116 of the image acquisition device 102.

Figure 3:
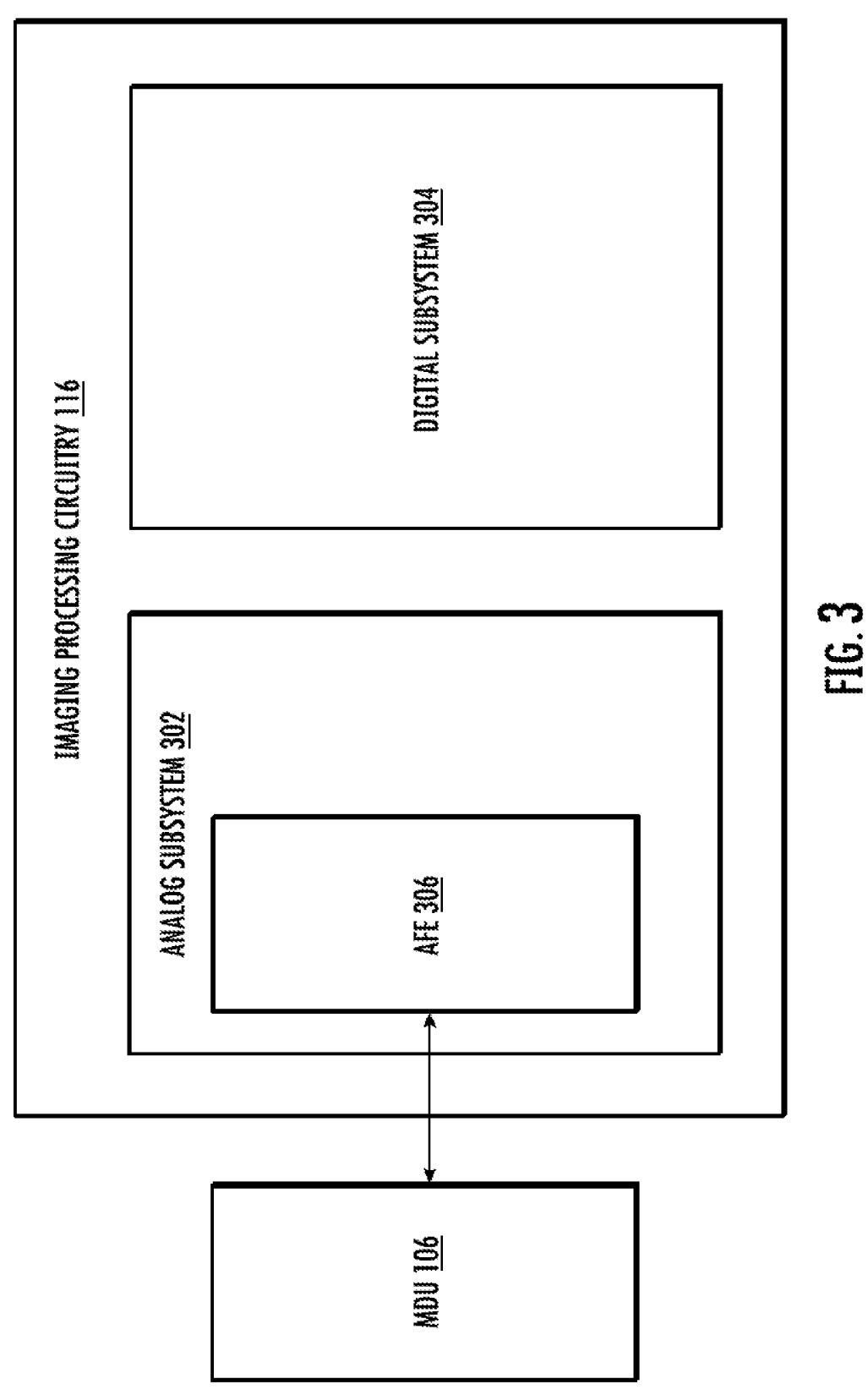
FIG. 3 illustrates an embodiment of yet another portion of the intravascular imaging system of FIG. 1 in greater detail.

FIG. 3 illustrates an embodiment of the imaging processing circuitry 116 of the IVUS imaging system 100 of FIG. 1. As can be seen from this figure, the imaging processing circuitry 116 includes both an analog subsystem 302 and a digital subsystem 304. Further, the analog subsystem 302 includes at least an analog front end (AFE) 306. The analog front end (AFE) 306 couples to the MDU 106 and receives signals from the IVUS catheter 104.

Figure 4:
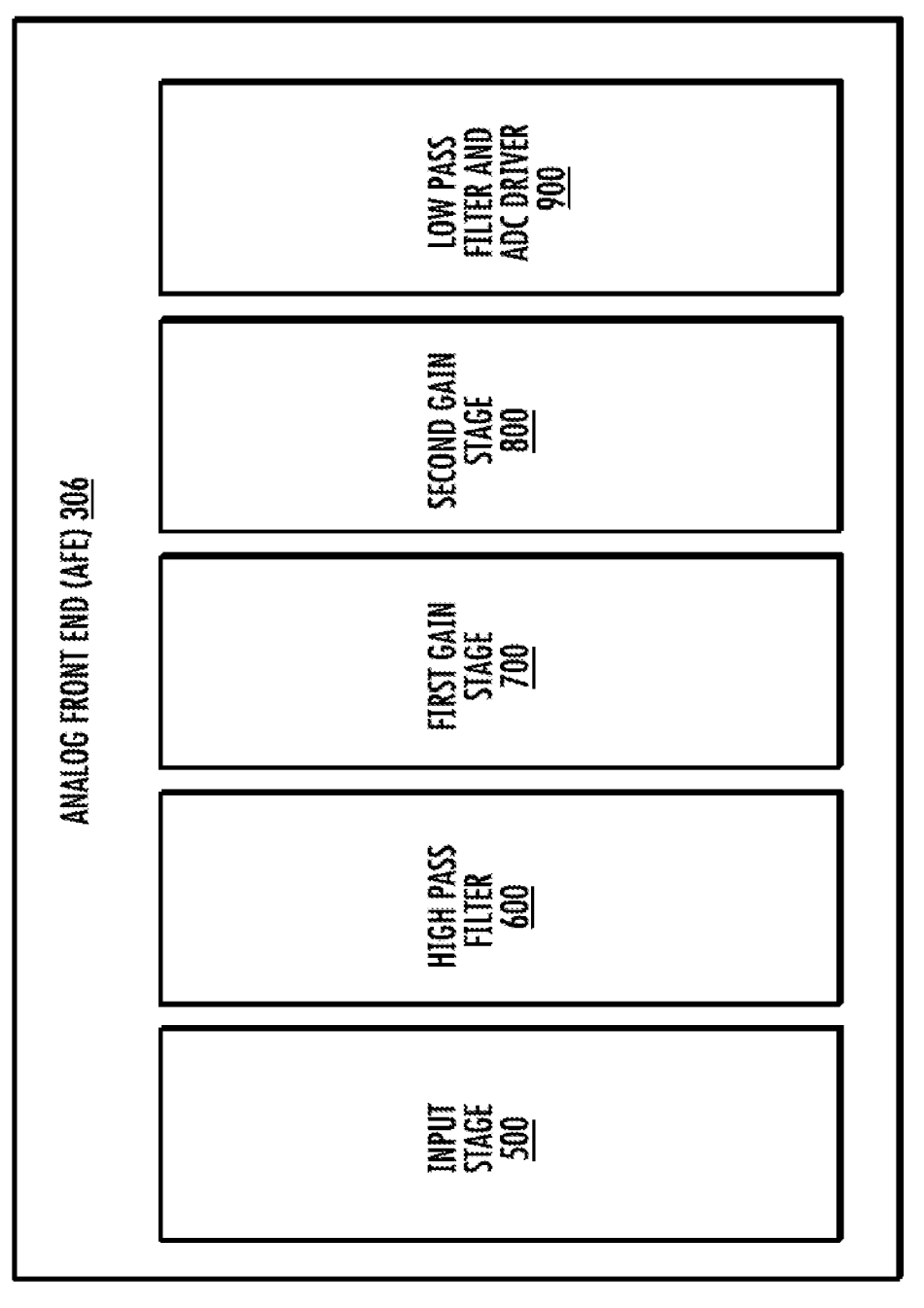
FIG. 4 illustrates an embodiment of an analog front end (AFE).

FIG. 4 illustrates an embodiment of the AFE 306. As depicted, the AFE 306 includes several stages or blocks. In particular, the AFE 306 includes an input stage 500, a high pass filter 600, a first gain stage 700, a second gain stage 800, and a low pass filter and ADC driver 900. It is important to note that an advantage of the present disclosure, which will be described in greater detail below, is that each stage or block of AFE 306 includes multiple pathways to accommodate various bandwidth imaging devices (e.g., legacy IVUS devices, next generation IVUS devices, etc.). These pathways can either be dynamically controlled or can be set at manufacturing. However, of note, the AFE 306 will not need to be reengineered and a new circuit board will not need to be manufactured to support a change in the imaging devices with which AFE 306 supports.

Figure 5:
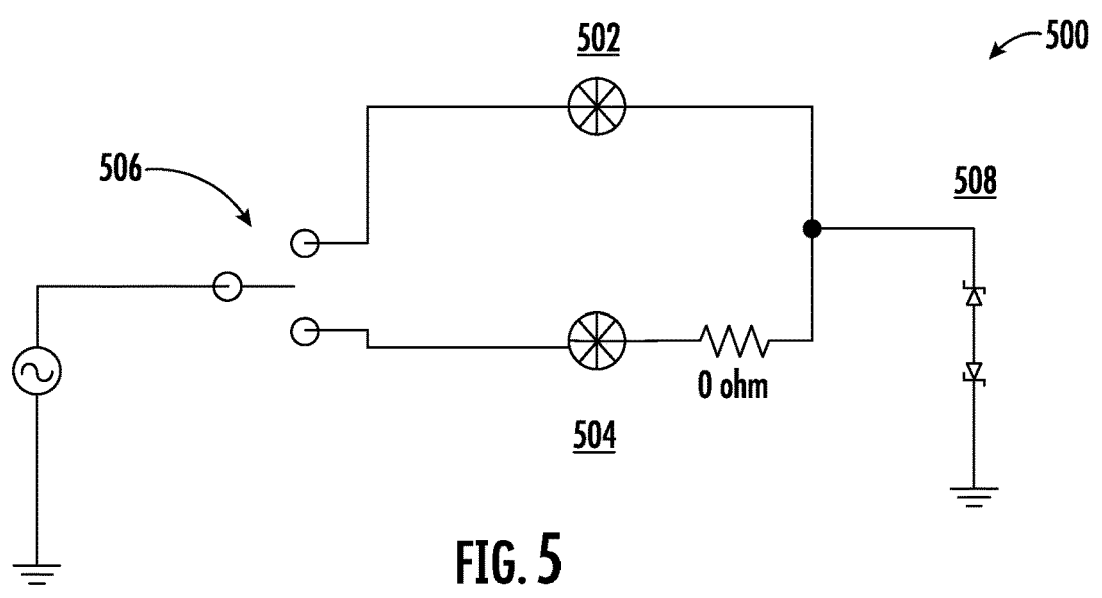
FIG. 5 illustrates an embodiment of an input stage of an AFE.

FIG. 5 illustrates a circuit diagram of an embodiment of the input stage 500 of AFE 306. With some embodiments, AFE 306 can include one or more signal pathways to acquire the return signal from the IVUS catheter 104 (e.g., return signals captured by the transducers 202 and transmitted to the MDU 106). For example, the input stage 500 can include a first connector 502, a second connector 504, or both the first connector 502 and the second connector 504. With some embodiments, the first connector 502 can be a Lemo connector configured to couple to an RF signal line (e.g., MDU bus 110, or the like). In some embodiments, the second connector 504 can be a subminiature version A (SMA) connector configured to couple to an RF signal line (e.g., MDU bus 110, or the like). Where more than one connector (e.g., first connector 502 and second connector 504, or the like) are provided in input stage 500, input stage 500 can include a switch 506 to toggle between the first connector 502 and second connector 504. It is noted that with some examples, the input stage 500 can include multiple connectors to facilitate allowing a test engineer flexibility in testing the AFE 306 without a custom cable assembly or fixture and instead leveraging off the shelf cables (e.g., SMA connectors, etc.).

The input stage 500 further includes a transient voltage suppressor diode, such as, TVS diode 508. With some embodiments, the TVS diode 508 can be a low capacitance TVS diode and can be included in the input stage 500 to mitigate the risk of electronic static discharge.

Figure 6:
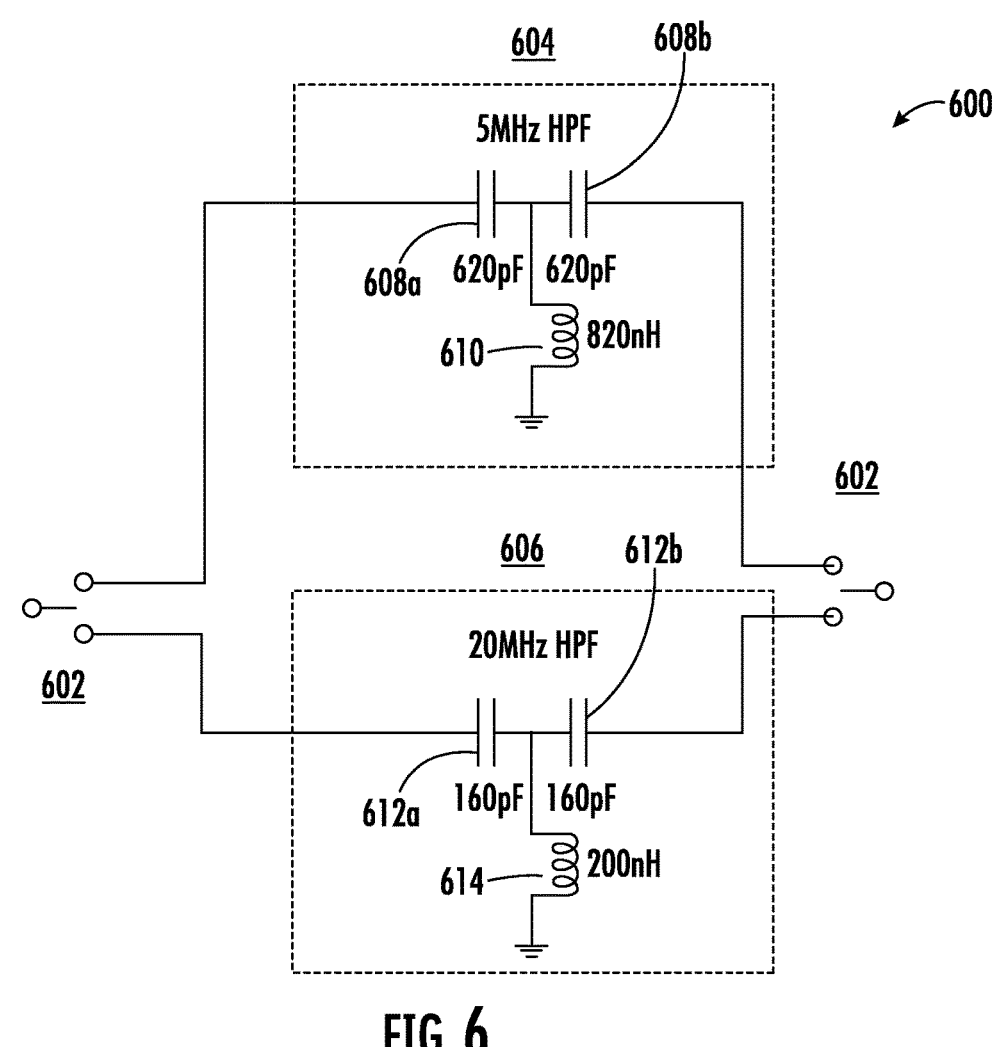
FIG. 6 illustrates an embodiment of a high-pass filter stage of an AFE.

FIG. 6 illustrates a circuit diagram of an embodiment of the high pass filter 600 of AFE 306. The high pass filter 600 includes switches 602, which can be controlled by, for example, other subsystems 120 of image acquisition device 102. The switches 602 can be used to select between high pass filter 604 and high pass filter 606 of high pass filter 600. High pass filter 600 is provided with two high pass filters having different characteristics. As depicted, high pass filter 604 is a 5 megahertz (MHz) filter having two 620 picofarad (pF) capacitors 608a and 608b and an 820 nanohenry (nH) inductor 610. Conversely, the high pass filter 606 is a 20 MHz filter having two 160 pF capacitors 612a and 612b and an 820 nH inductor 614.

In some examples, the high pass filter 604 can be between a 0 MHZ (short circuit to pass through a signal without filtering) and 12 MHz high-pass filter while the high pass filter 606 can be between a 15 and 30 MHz high-pass filter.

As noted above, the high pass filter 600 stage of AFE 306 includes multiple "pathways" (e.g., a first pathway through the high pass filter 604, a second pathway through the high pass filter 606, etc.) which is selected by switches 602. Further as noted, switches 602 can be coupled to and/or controlled by other subsystems 120 (e.g., a FPGA of other subsystems 120, or the like) and dynamically adjusted to change which pathway is selected based on the type of imaging device (e.g., IVUS catheter 104) is coupled to MDU 106. As an example, where IVUS catheter 104 is a legacy (or lower bandwidth) IVUS catheter, switches 602 can be configured (e.g., by other subsystems 120) to select high pass filter 604 while where IVUS catheter 104 is a next generation (or higher bandwidth) IVUS catheter, switches 602 can be configured (e.g., by other subsystems 120) to select high pass filter 606.

Figure 7A:
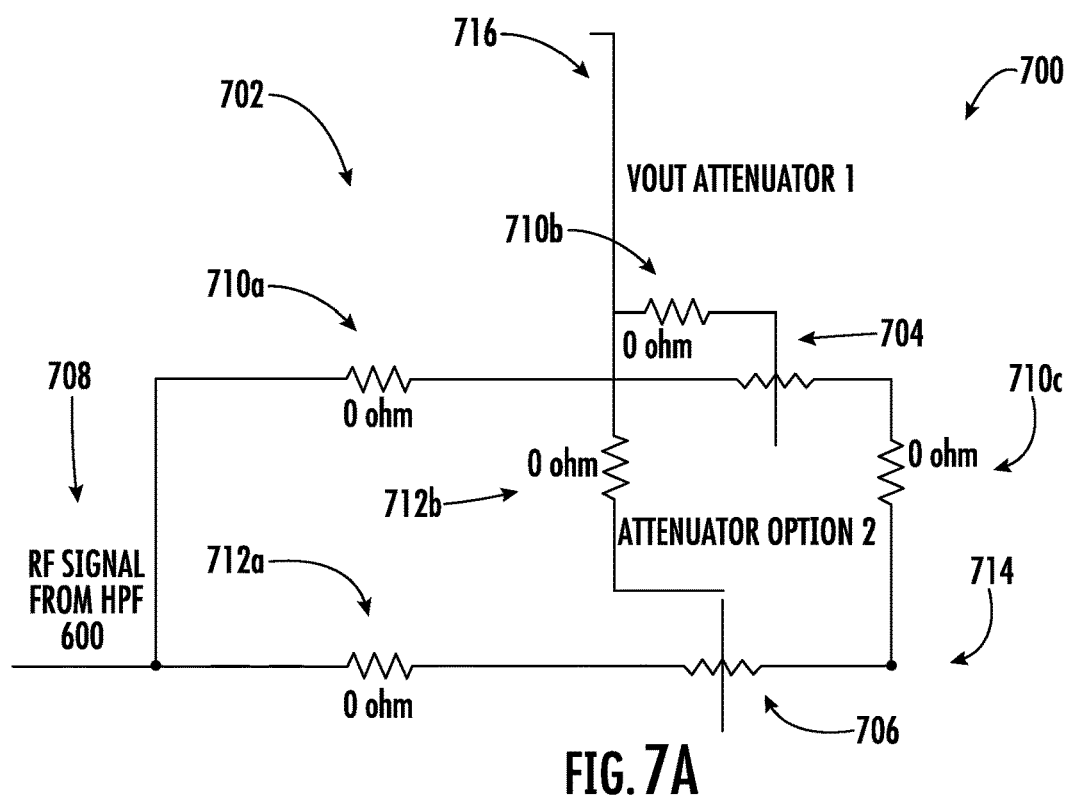
FIG. 7A illustrates an embodiment of a portion of a gain stage of an AFE.
Figure 7B:
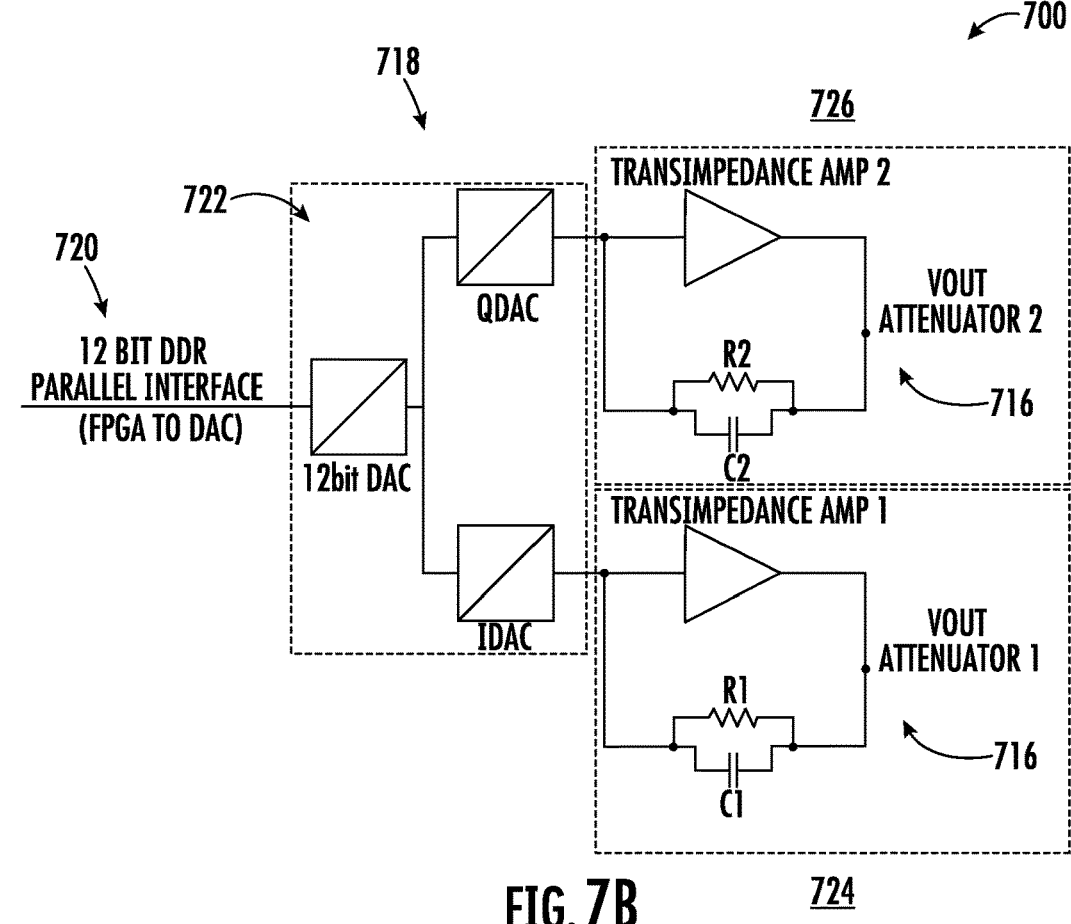
FIG. 7B illustrates an embodiment of another portion of a gain stage of an AFE.
Figure 7C:
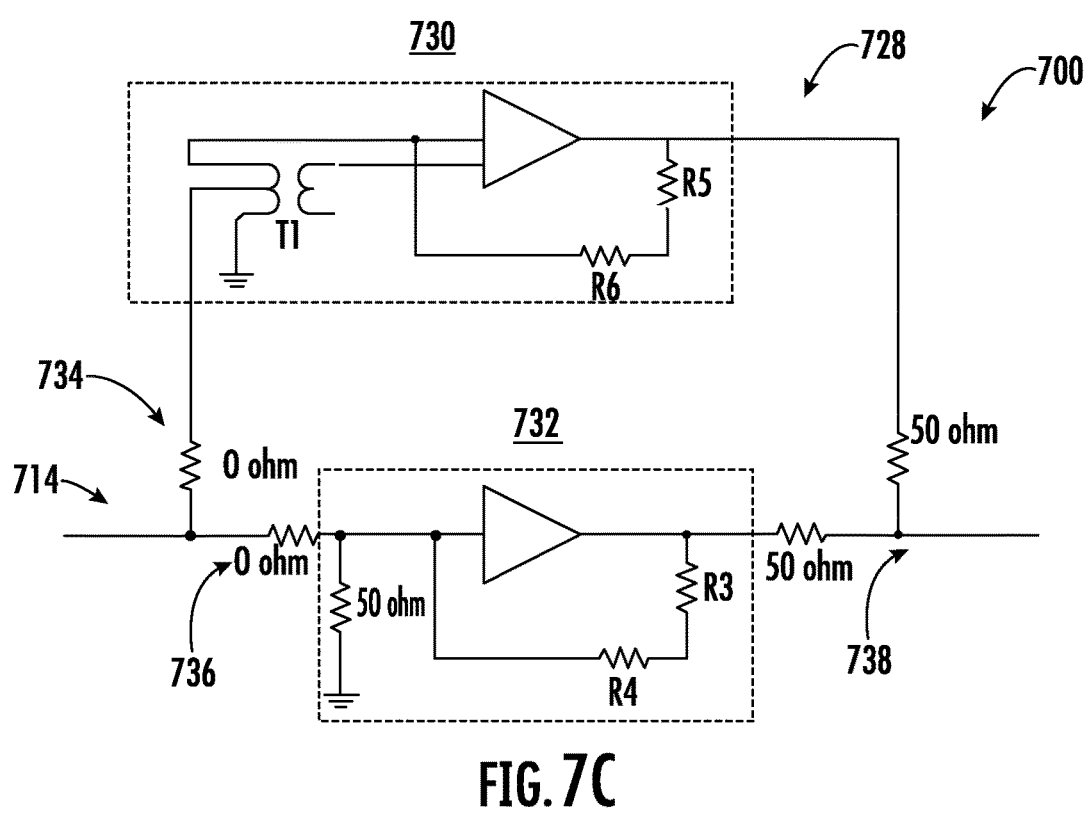
FIG. 7C illustrates an embodiment of yet another portion of a gain stage of an AFE.
Figure 7D:
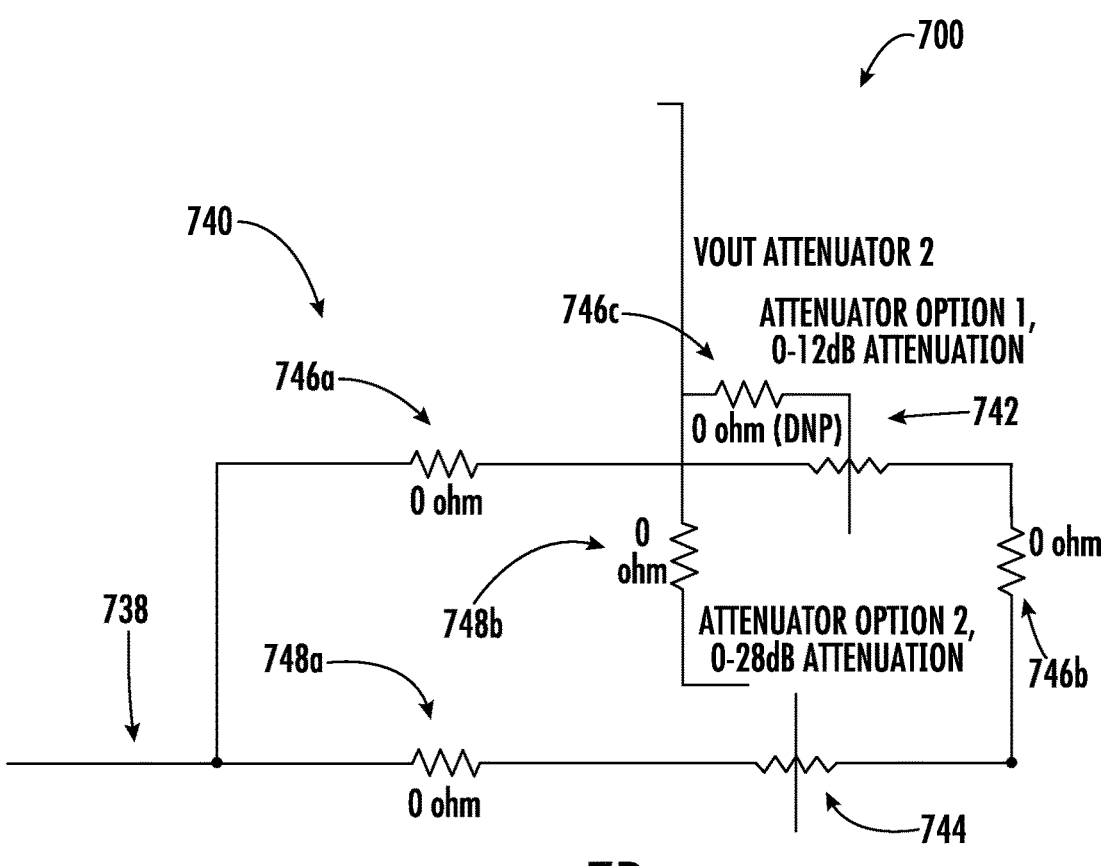
FIG. 7D illustrates an embodiment of still another portion of a gain stage of an AFE.

FIG. 7A, FIG. 7B, FIG. 7C, and FIG. 7D illustrate an embodiment of portions of first gain stage 700 of AFE 306. Prior to describing these figures in more detail, a high level overview of the first gain stage 700 is provided. In general, the signal from high pass filter 600 passes through one of two attenuators (e.g., FIG. 7A). The voltage controlled attenuators are configured by other subsystems 120 where the signal is fed into a transimpedance amplifier (e.g., FIG. 7B). From the attenuator stage, the signal travels through one of two high speed op-amps (e.g., FIG. 7C) and then through one of two radio frequency (RF) attenuators (e.g., FIG. 7D). Of note, the RF attenuators depicted in FIG. 7D are controlled in the same manner as the attenuators shown in FIG. 7A and FIG. 7B.

Turning more particularly to FIG. 7A, a circuit 702 is shown a pair of voltage attenuators (e.g., voltage attenuator 704 and voltage attenuator controller 706) are depicted. The portion of first gain stage 700 depicted here receives, at input 708, the RF signal from the high pass filter 600. This signal is routed through either the voltage attenuator 704 or voltage attenuator controller 706. Which voltage attenuator the signal is routed through can be set at manufacturing by soldering in jumpers (e.g., 0 ohm ($\Omega$) resistors) in either pathway resistors 710a, 710b, and 710c to select voltage attenuator 704 or in pathway resistors 712a and 712b to select voltage attenuator controller 706 and then the signal is communicated (e.g., at terminal 714) to the op-amps of first gain stage 700 shown in FIG. 7C. It is noted that the term "pathway resistor" is used interchangeably with jumper and jumper location herein. That is, the term jumper location is intended to mean the location of the pathway resistors (e.g., pathway resistor 710a, etc.) outlined herein while jumper is intended to mean where an electrical conductor (e.g., a 0Ω resistor, a conductive wire, or the like) is installed in the jumper location. It will be appreciated herein that the locations of the pathway resistors described herein will not all be installed but are provided to facilitate flexibility in selecting which sub-circuits are "active" or rather which circuits are and which are not coupled to inputs and outputs of each stage.

FIG. 7B illustrates a schematic of an embodiment of control circuitry for the voltage attenuators 704 and 706 of first gain stage 700. As depicted, the control side of voltage attenuators 704 and 706 are coupled to terminal 716 and either pathway resistor 710b or pathway resistor 712b is installed in the circuit depicted in FIG. 7A to complete the circuit to one of the voltage attenuators 704 or 706. The control signal can be generated from other subsystems 120 (e.g., an FPGA of other subsystems 120, or the like) and routed to terminal 716 via a circuit like the circuit depicted in FIG. 7B. FIG. 7B shows circuit 718 which receives as input, at DAC input 720, a digital control signal (e.g., a 12-bit dual data rate (DDR) control signal, or the like) from other subsystems 120. The digital signal received at DAC input 720 is fed through digital-to-analog converter 722 and then onto conditioning circuit 724 and conditioning circuit 726. The conditioning circuit 724 and conditioning circuit 726 each include an op-amp and resistor-capacitor (RC) circuit operating as a transimpedance amplifier. The output from the conditioning circuit 724 and conditioning circuit 726 is routed to terminal 716.

FIG. 7C illustrates an embodiment of a pair of high-speed op-amps depicted as circuit 728. Circuit 728 is configured to receive input from the output of the voltage attenuator 704 or 706 depicted in circuit 702 of FIG. 7A. Circuit 728 has input as terminal 714 and then pathways through one of a number of amplifier circuits (e.g., op-amp circuit 730 or op-amp circuit 732). The amplifier circuit with which the RF signal from the terminal 714 is routed through can be set at manufacturing by installing a jumper (e.g., 0Ω resistor) in either pathway resistor 734 or pathway resistor 736. The output from the set amplifier stage (e.g., op-amp circuit 730, op-amp circuit 732, etc.) is available at terminals 738, which is fed into the circuit 740 of FIG. 7D.

FIG. 7D illustrates circuit 740, which is another voltage attenuator circuit like the circuit 702 of FIG. 7A. Circuit 740 includes voltage attenuators 742 and 744 which can be selected based on installing jumpers (e.g., at pathway resistors 746a, 746b, and 746c or pathway resistors 748a and 748b) like described above in relation to circuit 702. Furthermore, although not depicted here, circuit 740 can be controlled in the same manner and with the same type of circuit as shown in FIG. 7B (e.g., circuit 718).

Figure 8A:
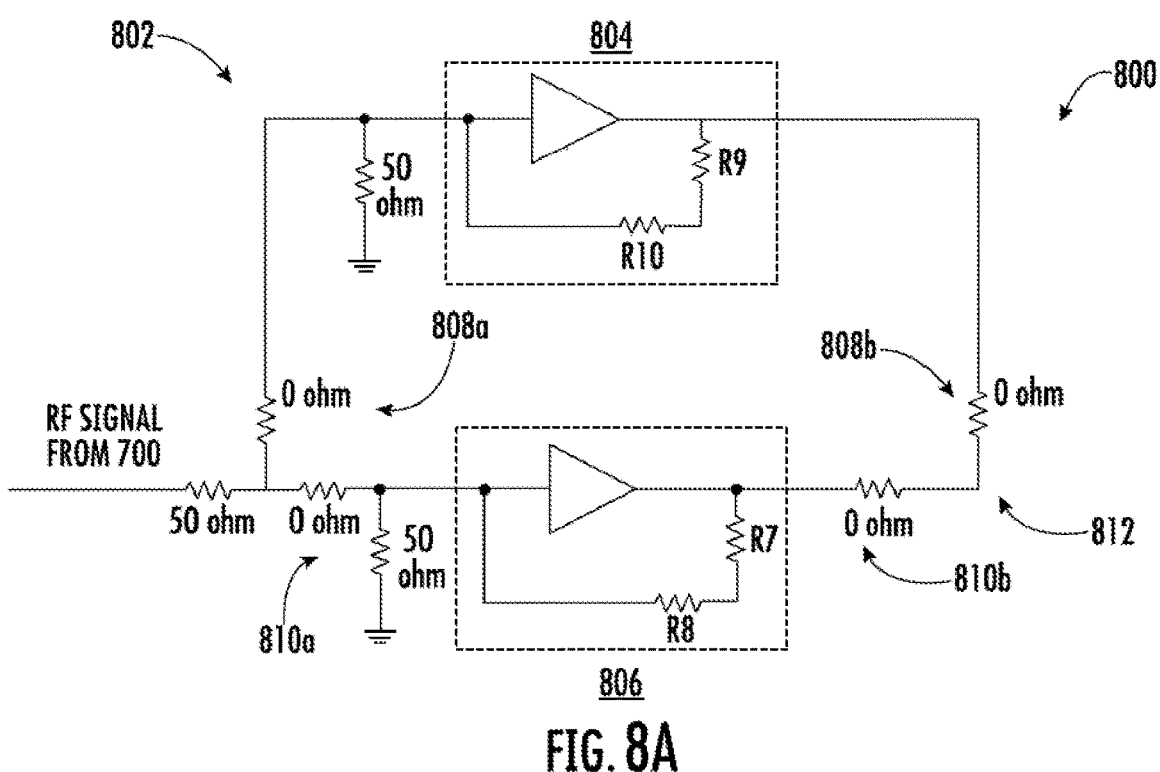
FIG. 8A illustrates an embodiment of a portion of another gain stage of an AFE.

The second gain stage 800 can be electrically coupled to the output of the first gain stage 700. In general, the second gain stage 800 includes a pair of amplifier circuits (e.g., FIG. 8A) through which the circuit can be completed at manufacturing and then a clipper amplifier stage (e.g., FIG. 8B). For example, as shown in FIG. 8A, circuit 802 includes amplifier circuit 804 and amplifier circuit 806, which correspond to alternative electrical pathways through circuit 802. The pathway is set at manufacturing by installing jumpers (e.g., 0Ω resistors, or the like) in either pathway resistors 808a and 808b or pathway resistors 810a and 810b. The amplifier circuits 804 and 806 each include an op-amp configured to amplify the RF signal different amounts. The circuit 802 has an output at terminal 812, which is the input to circuit 814.

Figure 8B:
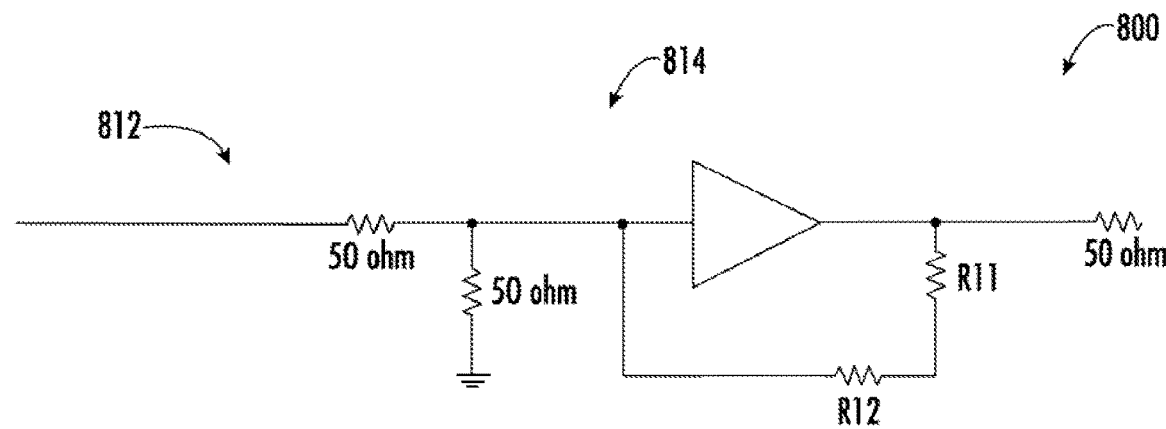
FIG. 8B illustrates an embodiment of another portion of the other gain stage of an AFE.

FIG. 8B illustrates an embodiment of a clipper circuit 814 which received input from circuit 802 at terminal 812 and includes an op-amp arranged in a clipper configuration.

Figure 9:
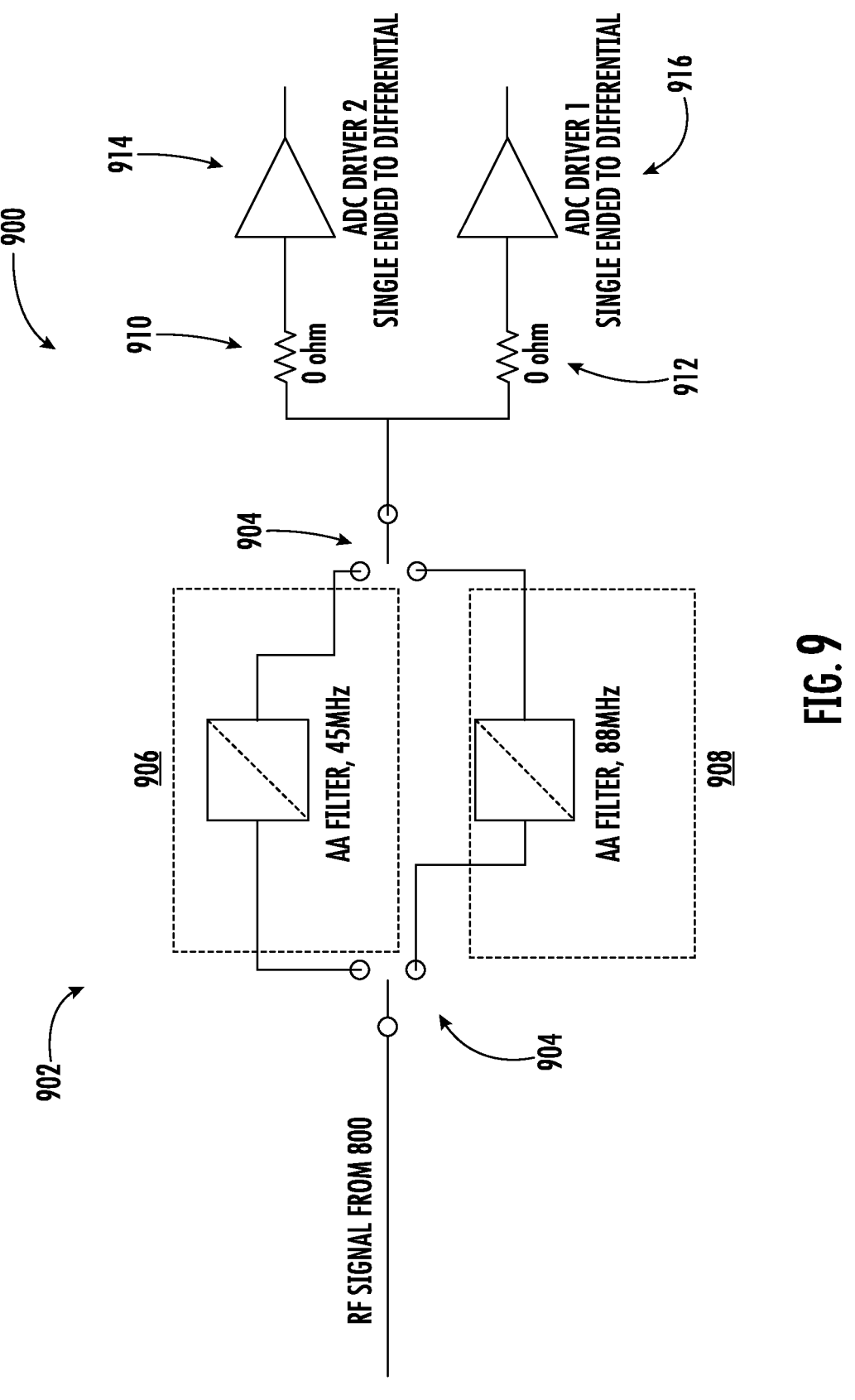
FIG. 9 illustrates an embodiment of a low-pass filter and analog to digital converter stage of an AFE.

FIG. 9 illustrates a circuit diagram circuit 902 of the low pass filter and ADC driver 900 of AFE 306 according to some embodiments. The low pass filter and ADC driver 900 includes switches switch 904, which can be controlled by, for example, other subsystems 120 of image acquisition device 102. The switches circuit 902 can be used to select between low pass filter 906 and low pass filter 908 of low pass filter and ADC driver 900. Low pass filter and ADC driver 900 is provided with two low-pass filters having different characteristics. As depicted, low pass filter 906 is a 45 megahertz (MHz) filter while low pass filter 908 is an 88 MHz filter.

Like the high pass filter 600 stage of AFE 306, low pass filter and ADC driver 900 includes multiple "pathways" (e.g., a first pathway through the low pass filter 906, a second pathway through the low pass filter 908, etc.) which is selected by switch 904. Further as noted, switches switch 904 can be coupled to and/or controlled by other subsystems 120 (e.g., a FPGA of other subsystems 120, or the like) and dynamically adjusted to change which pathway is selected based on the type of imaging device (e.g., IVUS catheter 104) is coupled to MDU 106. As an example, where IVUS catheter 104 is a legacy (or lower bandwidth) IVUS catheter, switch 904 can be configured (e.g., by other subsystems 120) to select low pass filter 906 while where IVUS catheter 104 is a next generation (or higher bandwidth) IVUS catheter, switch 904 can be configured (e.g., by other subsystems 120) to select low pass filter 908.

From the output of either low pass filter 906 or low pass filter 908, the circuit 902 includes multiple analog to digital converter (ADC) drivers, which can be selected at manufacturing by installing jumpers (e.g., 0Ω resistors, or the like) in pathway resistor 910 or pathway resistor 912 to complete the circuit pathway through either ADC driver 914 or ADC driver 916.

With some embodiments, the sampling frequency of the ADC driver 914 and/or ADC driver 916 can be 400 Mega-samples per second (MSPS), which may be 4.5 times the maximum frequency of the sampled signal. Accordingly, oversampling in such a manner may obviate the need to use an anti-aliasing filter. Some embodiments may provide a dynamically selectable anti-aliasing filter.

It is noted that selection of which ADC driver is used can be based on the bandwidth of the sampled signal (e.g., legacy, next generation, etc.). For example, both ADC driver 914 and ADC driver 916 may be capable of handling the RF signal, however each has a unique advantages over the other. For example, ADC driver 914 may provide a faster over-drive recovery (e.g., 1 nanosecond, or the like) that allows the system to better handle saturated signals (e.g., when plaque is detected). As another example, ADC driver 916 provides lower distortion and lower noise so should present a clearer image in comparison with the ADC driver 914.

Figure 10:
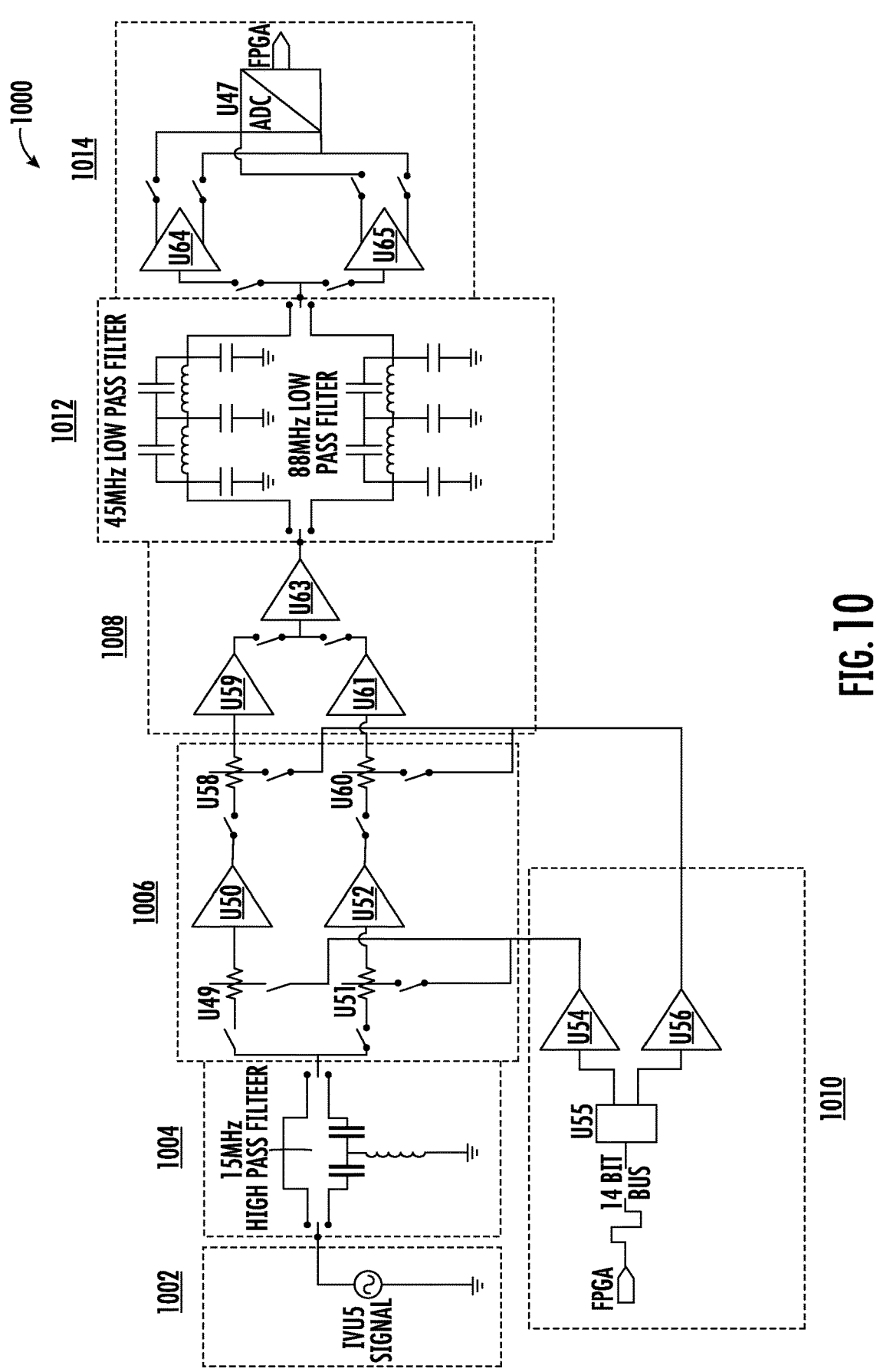
FIG. 10 illustrates an embodiment of an AFE.

FIG. 10 illustrates a circuit diagram an AFE 1000, which can be implemented as AFE 306. As depicted, AFE 1000 includes multiple sub-stages or blocks. AFE 1000 includes input stage 1002, high-pass filter 1004, gain stage 1006, gain stage 1008, gain stage controller 1010, low-pass filter 1012, and ADC 1014. With some embodiments, gain stage 1006 and gain stage 1008 can be combined into a single gain stage. With some examples, input stage 1002 can be like input stage 500 shown in FIG. 5; high-pass filter 1004 can be like high pass filter 600 shown in FIG. 6; gain stage 1006 and gain stage controller 1010 can be like the first gain stage 700 shown in FIG. 7A, FIG. 7B, FIG. 7C, and FIG. 7D; gain stage 1008 can be like second gain stage 800 shown in FIG. 8A and FIG. 8B; and low-pass filter 1012 and ADC 1014 can be like low pass filter and ADC driver 900 shown in FIG. 9.

Terms used herein should be accorded their ordinary meaning in the relevant arts, or the meaning indicated by their use in context, but if an express definition is provided, that meaning controls.

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to one or multiple ones. Additionally, the words "herein," "above," "below" and words of similar import, when used in this application, refer to this application as a whole and not to any portions of this application. When the claims use the word "or" in reference to a list of two or more items, that word covers all the following interpretations of the word: any of the items in the list, all the items in the list and any combination of the items in the list, unless expressly limited to one or the other. Any terms not expressly defined herein have their conventional meaning as commonly understood by those having skill in the relevant art(s).

What is claimed is:

1. An analog front end (AFE) for an intracorporeal image acquisition device, comprising:

a high-pass filter stage, the high-pass filter stage comprising a plurality of high-pass filters and at least one switch selectable to electrically couple one of the plurality of high-pass filters to an input;

a gain stage comprising:

a plurality of voltage attenuators, a plurality of amplifiers circuits, and a plurality of jumper locations, wherein one or more jumpers are installed in at least one but not all of the plurality of jumper locations to electrically couple one of the plurality of voltage attenuators to an output from the high-pass filter stage and to electrically couple an output from the one of the plurality of voltage attenuators to a one of the plurality of amplifier circuits; and a low-pass filter stage comprising a plurality of low-pass filters and at least one switch selectable to electrically couple one of the plurality of low-pass filters to an output from the gain stage.

2. The AFE of claim 1, wherein the plurality of high-pass filters comprise a first high-pass filter and a second high-pass filter, wherein the first high-pass filter is between a 0 and 12 megahertz high-pass filter, and wherein the second high-pass filter is between a 15 and 30 megahertz high-pass filter.

3. The AFE of claim 2, wherein at least one switch of the high-pass filter stage comprises a first switch and a second switch and wherein the first switch and the second switch are configured to be dynamically controlled by a controller circuit and arranged to electrically couple the input to the analog front end to a selected one of either the first high-pass filter or the second high-pass filter and to electrically couple the output from the selected one of either the first high-pass filter or the second high-pass filter to the output of the high-pass filter stage.

4. The AFE of claim 3, wherein the first high-pass filter and the second high-pass filter are T high-pass filters comprising a pair of capacitors in arranged in series and an inductor electrically coupled between ground and the center of the pair of capacitors.

5. The AFE of claim 1, wherein the plurality of voltage attenuators of the gain stage comprise a first voltage attenuator and a second voltage attenuator, wherein the first voltage attenuator is a 12 decibel voltage attenuator, and wherein the second voltage attenuator is a 28 decibel voltage attenuator.

6. The AFE of claim 5, wherein the gain stage further comprises a digital to analog converter and at least one transimpedance amplifier, wherein the transimpedance amplifier is electrically coupled to a control input of either the first voltage attenuator or the second voltage attenuator based on the one or more jumpers.

7. The AFE of claim 5, wherein the plurality of amplifier circuits comprises a first amplifier circuit and a second amplifier circuit, wherein the first amplifier circuit comprises an inductor, an operation amplifier (op-amp), and a plurality of resistors arranged to form an amplifier circuit, and wherein the second amplifier circuit comprises an op-amp and a plurality of resistors arranged to form an amplifier circuit.

8. The AFE of claim 1, wherein the plurality of voltage attenuators comprise a first pair of voltage attenuators and a second pair of voltage attenuators and wherein one of the amplifier circuits is electrically coupled between the first one of the first pair of voltage attenuators and a first one of the second pair of voltage attenuators based on the one or more jumpers.

9. The AFE of claim 1, wherein the gain stage comprises a first gain stage and a second gain stage, wherein the second gain stage comprises a clipping operational amplifier (op-amp).

10. The AFE of claim 9, wherein the second gain stage further comprises a first amplifier circuit, a second amplifier circuit, and a plurality of pairs of jumper locations, wherein a pair of jumpers are installed in one of the plurality of pairs of jumper locations to electrically couple an input to the second gain stage to either a selected one of the first amplifier or the second amplifier and to electrically couple the output of the selected one of the first amplifier or the second amplifier to the clipping op-amp.

11. The AFE of claim 1, wherein the plurality of low-pass filters comprise a first low-pass filter and a second low-pass filter, wherein the first low-pass filter is less than or equal to a 60 megahertz low-pass filter, and wherein the second low-pass filter is greater than a 60 megahertz low-pass filter.

12. The AFE of claim 1, comprising at least one analog to digital converter (ADC) drivers.

13. An intracorporeal image acquisition device comprising:

image acquisition circuitry comprising an analog front end (AFE) and a digital processing circuit coupled to the AFE, the digital processing circuit arranged to receive a digitized signal from the AFE, the AFE comprising:

a high-pass filter stage, the high-pass filter stage comprising a plurality of high-pass filters and at least one switch selectable to electrically couple one of the plurality of high-pass filters to an input;

a gain stage comprising:

a plurality of voltage attenuators, a plurality of amplifiers circuits, and a plurality of jumper locations, wherein one or more jumpers are installed in at least one but not all of the plurality of jumper locations to electrically couple one of the plurality of voltage attenuators to an output from the high-pass filter stage and to electrically couple an output from the one of the plurality of voltage attenuators to a one of the plurality of amplifier circuits; and a low-pass filter stage comprising a plurality of low-pass filters and at least one switch selectable to electrically couple one of the plurality of low-pass filters to an output from the gain stage.

14. The intracorporeal image acquisition device of claim 13, wherein the plurality of high-pass filters comprise a first high-pass filter and a second high-pass filter, wherein the first high-pass filter is between a 0 and 12 megahertz high-pass filter, and wherein the second high-pass filter is between a 15 and 30 megahertz high-pass filter.

15. The intracorporeal image acquisition device of claim 14, wherein at least one switch of the high-pass filter stage comprises a first switch and a second switch and wherein the first switch and the second switch are configured to be dynamically controlled by a controller circuit and arranged to electrically couple the input to the analog front end to a selected one of either the first high-pass filter or the second high-pass filter and to electrically couple the output from the selected one of either the first high-pass filter or the second high-pass filter to the output of the high-pass filter stage.

16. The intracorporeal image acquisition device of claim 15, wherein the first high-pass filter and the second high-pass filter are T high-pass filters comprising a pair of capacitors in arranged in series and an inductor electrically coupled between ground and the center of the pair of capacitors.

17. The intracorporeal image acquisition device of claim 13, wherein the plurality of voltage attenuators of the gain stage comprise a first voltage attenuator and a second voltage attenuator, wherein the first voltage attenuator is a 12 decibel voltage attenuator, and wherein the second voltage attenuator is a 28 decibel voltage attenuator.

\* \* \* \* \*